(12) United States Patent
Dell'Orso

(10) Patent No.: US 11,187,770 B2
(45) Date of Patent: Nov. 30, 2021

(54) METHOD FOR ELIMINATING ALIASING ARTIFACTS IN A MAGNETIC RESONANCE IMAGE

(71) Applicant: Andrea Dell'Orso, Poggibonsi (IT)

(72) Inventor: Andrea Dell'Orso, Poggibonsi (IT)

( * ) Notice: Subject to any disclaimer, the term of this patent is extended or adjusted under 35 U.S.C. 154(b) by 0 days.

(21) Appl. No.: 16/962,866

(22) PCT Filed: Jan. 15, 2019

(86) PCT No.: PCT/IB2019/050290
§ 371 (c)(1),
(2) Date: Jul. 17, 2020

(87) PCT Pub. No.: WO2019/142092
PCT Pub. Date: Jul. 25, 2019

(65) Prior Publication Data
US 2020/0348383 A1  Nov. 5, 2020

(30) Foreign Application Priority Data

Jan. 19, 2018  (IT) .......................... 102018000001367

(51) Int. Cl.
*G01R 33/565* (2006.01)
*A61B 5/055* (2006.01)
(52) U.S. Cl.
CPC ........ *G01R 33/56545* (2013.01); *A61B 5/055* (2013.01)
(58) Field of Classification Search
CPC .......................... G01R 33/56545; A61B 5/055
See application file for complete search history.

(56) References Cited

U.S. PATENT DOCUMENTS

| | | | |
|---|---|---|---|
| 2015/0177353 A1* | 6/2015 | Setsompop | G01R 33/4826 324/309 |
| 2015/0241534 A1* | 8/2015 | Park | G01R 33/5611 382/131 |
| 2019/0361080 A1* | 11/2019 | Nittka | G01R 33/5608 |

FOREIGN PATENT DOCUMENTS

WO  2012090162 A1  7/2012

OTHER PUBLICATIONS

International Search Report, dated Mar. 20, 2019, corresponding to International Application No. PCT/IB2019/050290.

(Continued)

*Primary Examiner* — Gregory H Curran
(74) *Attorney, Agent, or Firm* — Ladas & Parry LLP; Malcolm J. MacDonald

(57) ABSTRACT

Method for eliminating aliasing artifacts in a magnetic resonance image, comprising the steps of obtaining a first and a second starting image (100a,100b) obtained by a determined acquisition sequence and using, respectively a phase encoding for columns, and a phase encoding for rows. Both the first and the second starting image (100a,100b) are organized in according to a matrix structure (m·n) comprising a plurality of portions (101a,101b) arranged according to m rows and n columns, each of which is associated to a respective numerical value corresponding to the light intensity of the portion. The method provides a translation step for translating at least one between the first and the second starting image (100a,100b) with respect to a respective reference system, in such a way to minimize the differences among the numerical values of the homologous portions of the first and of the second starting image due to the fact that the first and the second starting image are obtained by a different encoding phase.

3 Claims, 4 Drawing Sheets

(56) References Cited

OTHER PUBLICATIONS

Hamilton, C. A. et al: "Crisscross" MR Imaging: Improved Resolution by Averaging Signals with Swapped Phase-Encoding Axes, Radio, Radiological Society of North America, Inc, US, vol. 193, No. 1, Oct. 1994 (Oct. 1994), pp. 276-279, XP009149721.

Wang, H. et al.: "Cross Sampled Nonlinear GRAPPA for Parallel MRI", Proceedings of the International Society for Magnetic Resonance in Medicine, 20th Annual Meeting & Exhibition, May 5, 2012 (May 5, 2012), p. 2225, XP040624647.

\* cited by examiner

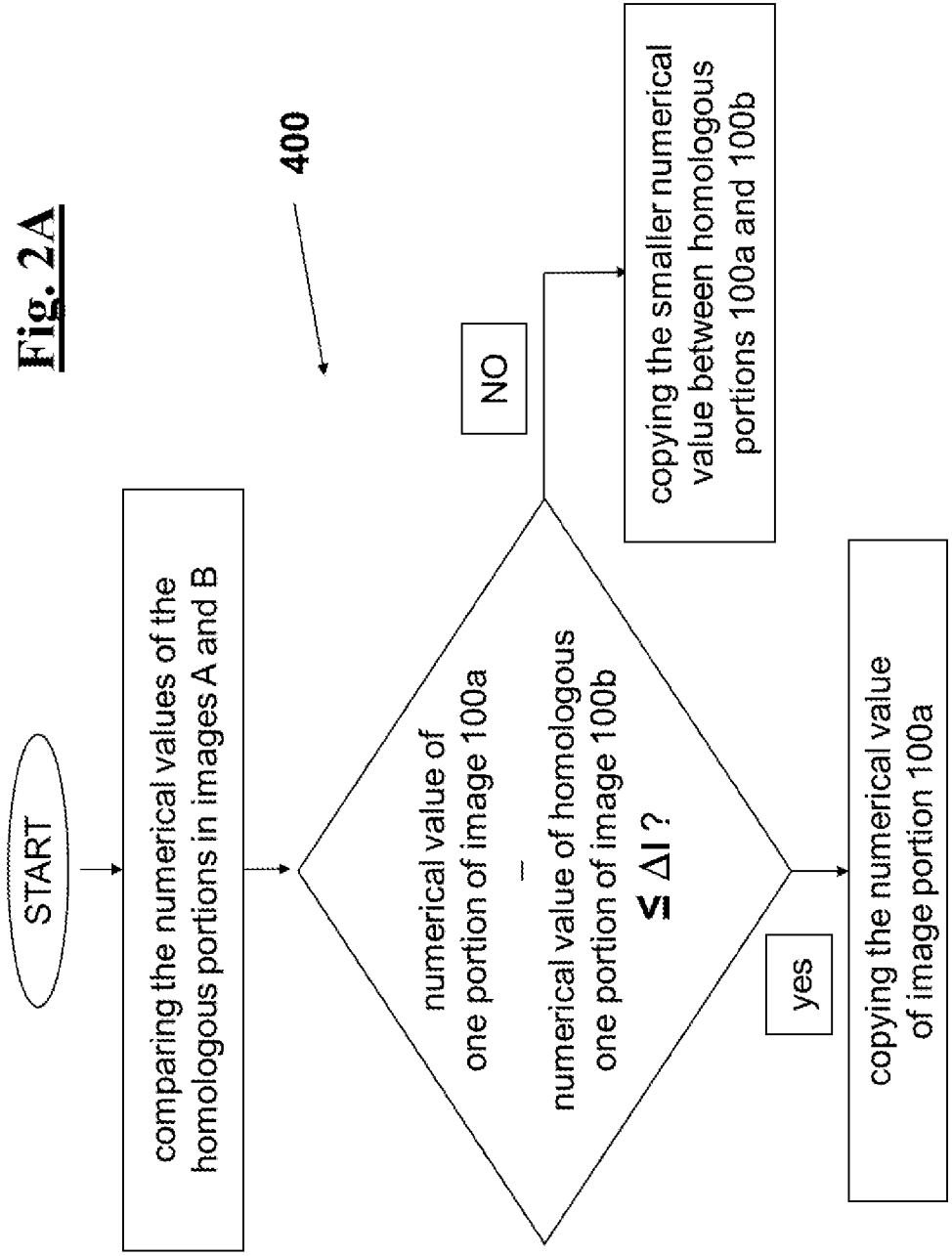

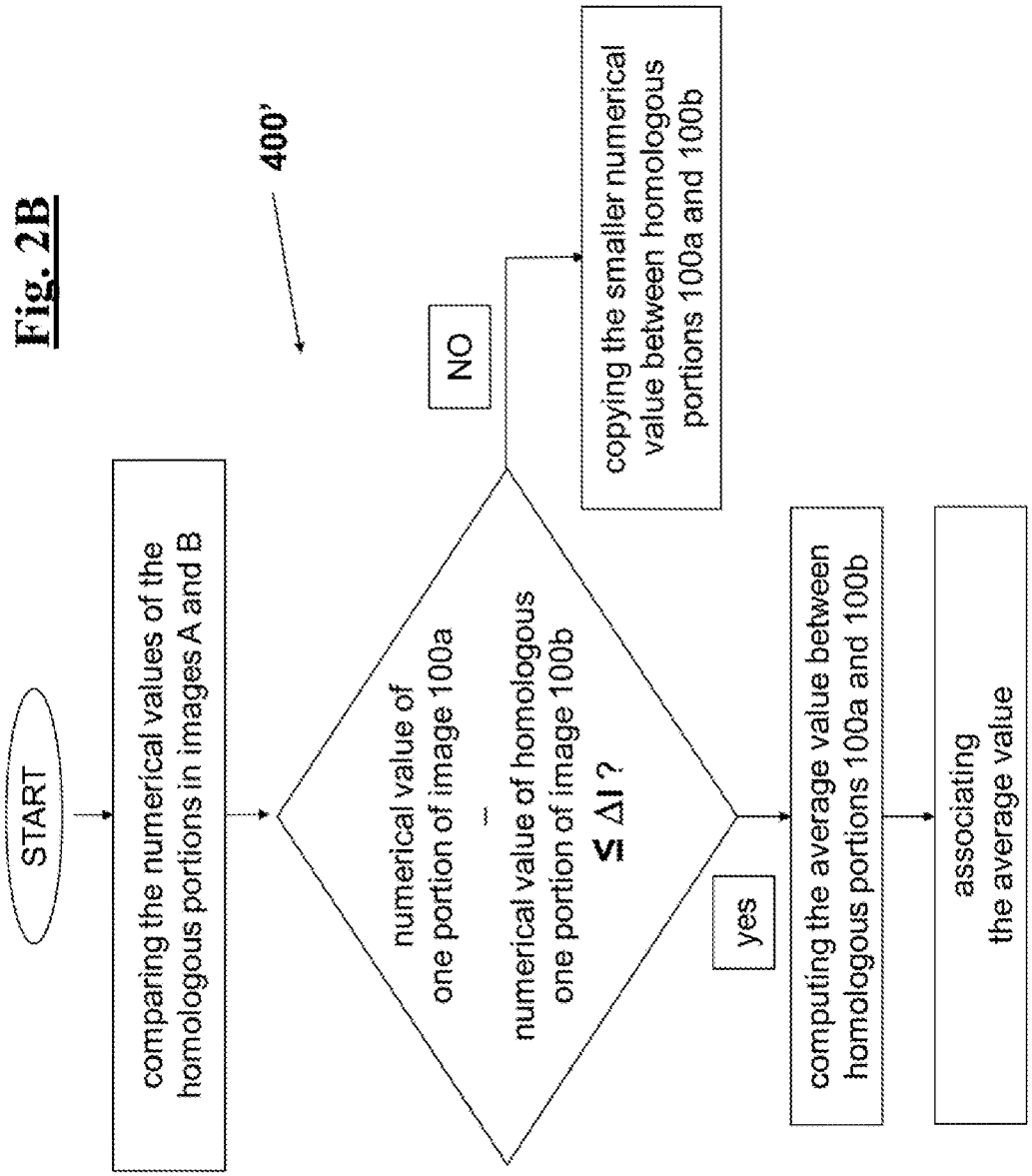

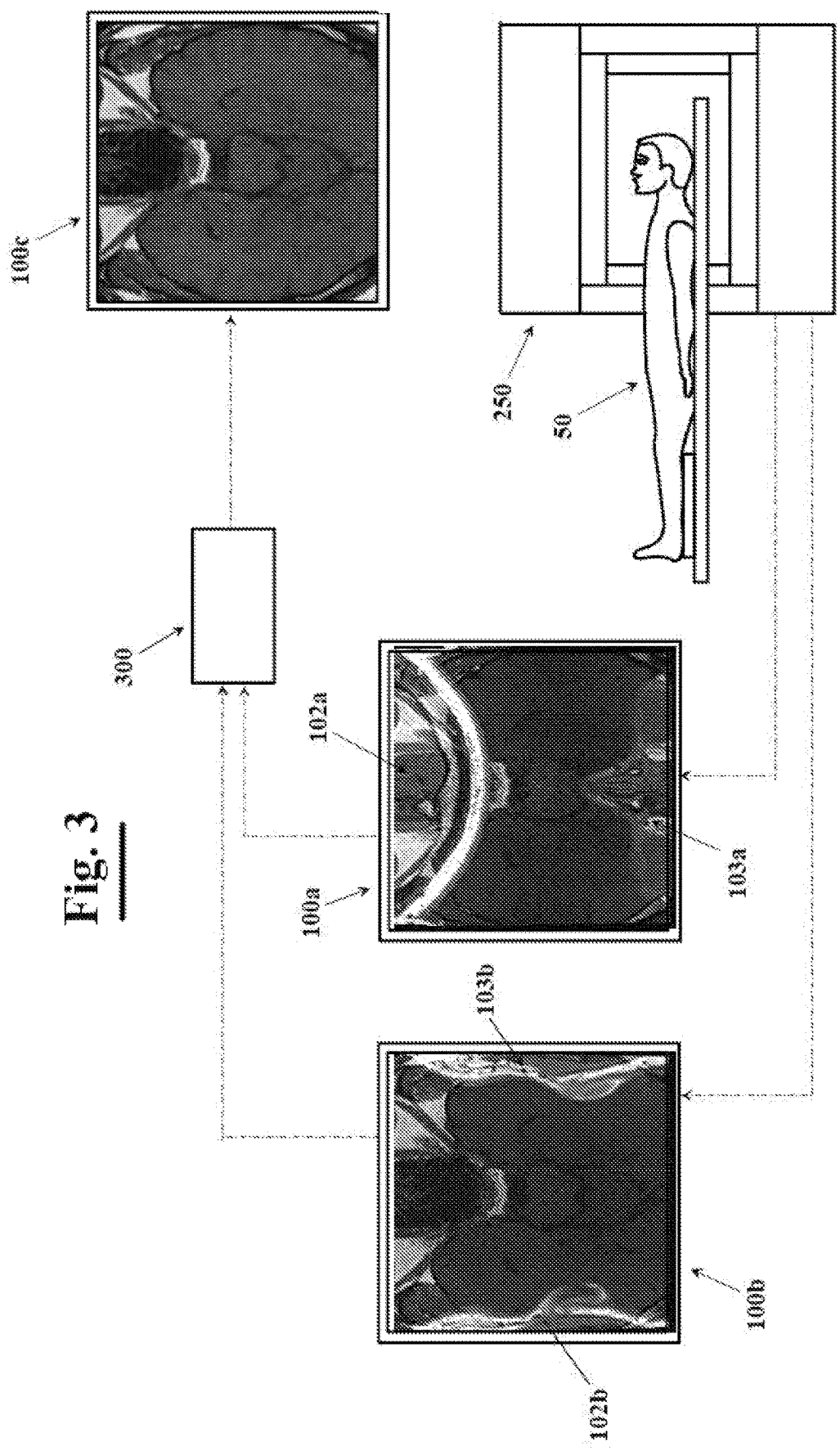

METHOD FOR ELIMINATING ALIASING ARTIFACTS IN A MAGNETIC RESONANCE IMAGE

FIELD OF THE INVENTION

The present invention relates to the field of processing magnetic resonance images and, in particular, relates to a method for eliminating aliasing artifacts in a magnetic resonance image.

DESCRIPTION OF THE PRIOR ART

As known, the term "artifact" indicates a noise, i.e. an imperfection, or characteristic, which appears in a magnetic resonance image, but that is not really present in the examined patient, or, in the case of diagnostic images, in the examined anatomical part. Sometimes the artifact is due to a malfunction of the machines, other times is the consequence of natural activities of determined anatomical regions of the human body. In any case, if artifacts are present on an image, they can compromise the correct examination of the examined anatomical part and can lead to a wrong diagnosis, for example because they hide a pathology.

A type of very common artifact in the magnetic resonance images is the artifact due to overturning, or overlapping, also known as "aliasing". This type of artifact consists in the re-projection of the parts positioned outside the "Field of View", or FOV, of the image and occurs when the field of view along the phase encoding direction is smaller than the entire object. An artifact of "aliasing" type is, for example, produced when in order to examine in detail the anatomical part of interest it is necessary to enlarge a determined region of a reference image. Analogously, an artifact of "aliasing" type is produced when the region of interest of the image in only a determined part of the examination plane of the anatomical part subjected to magnetic resonance. The method can be also applied to diagnostic images, which, besides providing a common artifact, provides also an artifact of aliasing type. In this case, the portions, i.e. the columns and/or the rows, which do not belong to the region of interest, produce the artifact. More precisely, in the image that is obtained by phase encoding for rows, the artifacts are caused by overlapping of the columns which do not belong to the region of interest. Analogously, in the image that is obtained by phase encoding for columns, the artifacts are produced by overlapping of the rows which do not belong to the region of interest.

In all the cases above described, the propagation direction of the artifact depends on the parameter "PHASE ENCODING DIRECTION" which is set by an operator in the management software of the apparatus before starting the acquisition sequence. The artifacts can, therefore, be seen in the phase encoding direction and appear as smudges, blurrings, or shadows of determined areas of the image. The presence of the artifacts in a magnetic resonance image can compromise the examination results, thus leading the doctor to a wrong diagnosis.

A method for eliminating artifacts in a magnetic resonance image is described in WO2012/090162 in the name of the same Applicant. The method starts with the step of obtaining a first image, acquired by using a phase encoding for columns, and a second image, which is, instead, acquired, by using a phase encoding for rows. The images that are so acquired are subjected to a processing sequence providing a comparative analysis for columns carried out by comparing the corresponding columns and computing the number of different portions, i.e. having a different intensity value. The images are, furthermore, subjected to an analysis for rows providing a comparison between the corresponding rows and computing the number of different portions, i.e. having different average intensity values. In this way, a first and a second I generation derived images are obtained, which are improved with respect to the starting images.

SUMMARY OF THE INVENTION

It is therefore an object of the present invention to provide a method to eliminate phase encoding artifacts, in particular artifacts due to overturning, or overlapping, also known as "aliasing artifacts", in a magnetic resonance image that allows to reduce the acquisition and processing time with respect to the known prior art methods, and that is able to guarantee a higher definition of the final image with respect to those methods.

This and other objects are achieved by the method, according to the invention, for eliminating aliasing artifacts in a magnetic resonance image, the method comprising the steps of:

obtaining a first starting image acquired by a determined acquisition sequence and using a phase encoding for columns, said first starting image being organized according to a matrix structure (m·n) comprising a plurality of portions arranged according to m rows and n columns, each portion of said plurality being associated to a respective numerical value corresponding to the bright intensity of said portion;

obtaining a second starting image acquired by said determined acquisition sequence used for obtaining said first starting image, but using a phase encoding for rows, said second starting image being organized according to a matrix structure (m·n) comprising a plurality of portions arranged according to m rows and n columns, each portion of said plurality being associated to a respective numerical value corresponding to the bright intensity of said portion;

whose main characteristic is to provide, furthermore, the steps of:

comparison of said numerical values of each portion of said first starting image with a homologous portion of said second starting image, i.e. occupying the same position in the respective matrix structure (m·n);

construction of a new matrix structure also this comprising a plurality of portions arranged according to m rows and n columns, said construction step comprising the steps of:

computing the difference of the numerical values of each couple of homologous portions of said first and of said second starting image;

association to a portion of said new matrix structure homologous to said portions of said first and of said second starting image the numerical value of the homologous portion corresponding to the first starting image, or of an average value of the numerical values of said homologous portions, if said difference is less than a predetermined threshold value ($\Delta I$), or, alternately, association to said portion of the smaller numerical value between the numerical value of said first and of said second homologous portion, if said difference is greater than said predetermined threshold value ($\Delta I$), iterating the above steps for each couple of homologous portions of said first and of said second starting image in such a way to obtain a new matrix structure corresponding to an improved magnetic resonance image;

and that before said comparing step, a translation step is provided for translating at least one between said first and said second starting image with respect to a respective reference system. In this way, it is possible to carry out a better comparative analysis due to the fact that the anatomical regions overlap each other and, therefore, the differences are minimized of numerical values among the homologous portions of the first and of the second starting images due to the fact that these are obtained by different encoding phases.

In particular, the above mentioned translation step can be carried out according to the results of a preliminary measurement step in which the numerical value is determined of each portion of the first and of the second starting image and of a following step of comparing the numerical values of the homologous portions.

Advantageously, the above mentioned preliminary measurement step comprises the steps of:

carrying out a plurality of determined translations of at least one between said first and said second starting image;

computing the mean squared error of the difference among the numerical values of the first and of the second starting image for each determined translation of the above mentioned plurality;

selecting the translation among the above mentioned plurality of translation steps corresponding to the smaller value of the computed mean squared error.

BRIEF DESCRIPTION OF THE DRAWINGS

The invention, now, will be shown with the following description of an exemplary embodiment of the same, exemplifying but not limitative, with reference to the attached drawings in which:

FIG. 2A shows a flow diagram in which the main steps of the method, according to the invention, are illustrated;

FIG. 2B shows a flow diagram in which the main steps of the method according to the invention in an alternative embodiment with respect to FIG. 2A;

FIG. 3 shows the application of the method, according to the invention, for eliminating aliasing artifacts in a real magnetic resonance image.

DESCRIPTION OF THE PREFERRED EMBODIMENT

Figure 1:
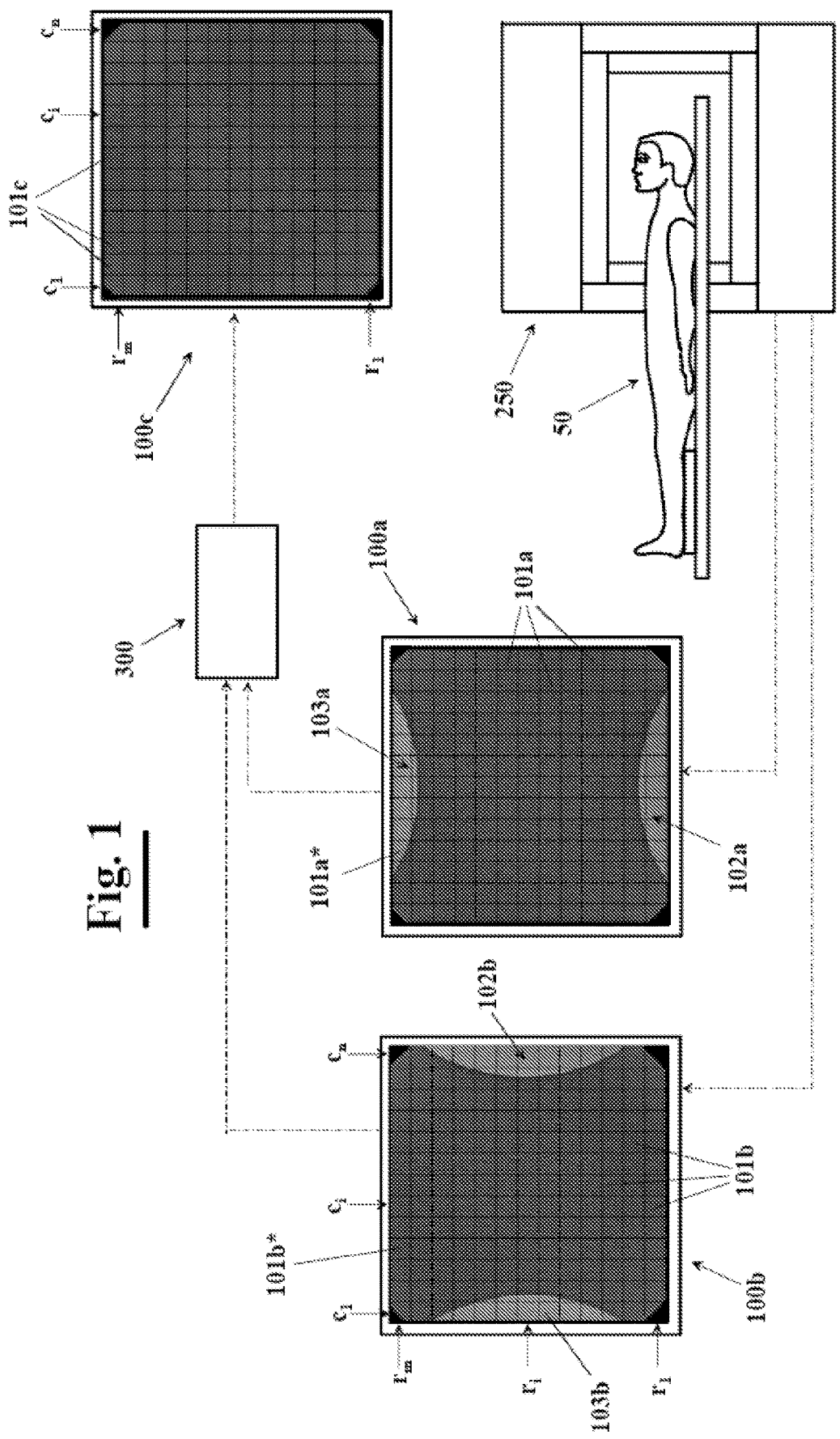
FIG. 1 diagrammatically shows the application of the method, according to the invention, for eliminating aliasing artifacts in a "cylindrical phantom" image of magnetic resonance.

With reference to FIG. 1, the method, according to the invention, for eliminating aliasing artifacts in an image, in particular a magnetic resonance image, starts with the steps of obtaining a first starting image 100a and a second starting image 100b. These are acquired at a same cross-section plane y and through a same acquisition sequence using identical instrumental variables of the machine as for example, the repetition time (TR), the echo time (TE), the inversion time (TI), the "flip angle" (θ), the pixel size, the field of view, or FOV, the layer thickness, or "window" (W), or "level" (L), but the first starting image 100a is acquired by using a phase encoding for columns and the second starting image 100b is acquired by using a phase encoding for rows. If the anatomical part of interest is subjected to a heart, or breathing, movement, the acquisition of the sequence can be carried out in "gate mode", that means synchronizing the acquisition by a electrocardiogram or by a detection device of thoracic extension due to the breathing. In this way, the image which has been acquired by phase encoding for rows and the image, which has been acquired by phase encoding for columns correspond to different instants, but the anatomical parts occupy the same position in the space.

In the example of FIG. 1, the starting images 100a and 100b are magnetic resonance images obtained by a magnetic resonance machine 250 for examining the state of health of an anatomical part of a patient 50. A skilled person in the art will have no difficulty to understand that the method according to the invention can be applied with the same advantages, also to magnetic resonance images of different type, as for example the magnetic resonance images of animal beings, vegetal species, objects of other type.

As known and diagrammatically shown in FIG. 1, each starting image 100a and 100b is provided by the processing software of the magnetic resonance machine 250 as divided in a determined number of portions 101a and 101b of determined dimensions, respectively, organized in a matrix structure (m·n), i.e. comprising m rows and n columns. The number of rows and columns is a parameter that can be set by an operator in a preliminary step. Each portion 101a and 101b of the above mentioned plurality is, furthermore, associated by the resonance machine 250 to a respective numerical value correlated to the light intensity of the same portion according to a known relation.

As shown in FIG. 1, the starting image 100a acquired with phase encoding for columns shows aliasing artifacts, 102a and 103a, which mainly propagate along a direction that is substantially parallel to the rows, whilst the starting image 100b, acquired with phase encoding for rows, shows aliasing artifacts 102b and 103b, which mainly propagate along a direction that is substantially parallel to the columns. In both the cases the aliasing 102a, 102b, 103a and 103b affect a determined number of respective portions 101a and 101b.

According to the present invention, once acquired, the starting images 100a and 100b are subjected to a sequence of processing steps, diagrammatically indicated with a block 300 in FIG. 1 and illustrated in a concise way in the flow diagram 400 of FIG. 2A, or 400' of FIG. 2B. More in detail, a comparison step is provided of the above mentioned numerical values of each portion 101a of the first starting image 100a with the homologous portion, i.e. occupying the same position in the respective matrix structure (m·n), of the second starting image 100b. In FIG. 1, for greater clearness, 2 homologous portions 101a* and 101b* are indicated that occupy in the respective images 100a and 100b the row m, in the case of FIG. 1 row 13, and column 4. The method, then, provides, a construction step of a new matrix structure (m·n) 100c constituted by respective portions 101c, each of which associated to a determined numerical value. More precisely, in a first embodiment of the method, shown in FIG. 2A, the new matrix structure 100c is obtained by associating to each portion 101c the numerical value of portion 101*a homologous to the same in the first starting image 100a, if the difference of the numerical values of the homologous portions 101a* and 101b* is less than a predetermined threshold value ΔI. Instead, if the difference of the numerical values of the homologous portions 101a* and 101b* is greater than the above mentioned predetermined threshold value, to portion 101*c is assigned the smaller numerical value between the numerical value of portion 101*a and 101b* homologous to the same, respectively in the first and in the second starting image 100a and 100b.

In the alternative embodiment of FIG. 2B, instead, the new matrix structure 100c is obtained by associating to each portion 101c, the average value of the numerical values of the portions 101*a and 101*b homologous to the same in the first and in the second starting image 100a and 100b, if the difference of the numerical values of the homologous portions 101a* and 101b* is less than a predetermined threshold value ΔI. By analogy to the embodiment of FIG. 2A, also in the alternative embodiment of FIG. 2B, if the difference of the numerical values of the homologous portions 101a* and 101b* is greater than the above mentioned predetermined threshold value, at the portion 101*c is assigned the smaller numerical value among those of the homologous portions 101*a and 101b*.

As can be immediately deduced by analysing the new matrix structure 100c, i.e. the image 100c that is obtained by applying the above method, according to the invention, to the starting images 101a and 101b, has allowed to completely eliminate the aliasing artifacts 102a, 102b, 103a, 103b and, therefore, to obtain a "clean" image and with a high noise reduction, more precisely a considerable improvement in the ratio signal/noise. As can be easily understood, even though in the description above, in practice the first starting image 100a is chosen as "reference image" for constructing the new matrix structure 100c, is however provided and, therefore, comprised in the present invention, also the possibility to choose as "reference image" the second starting image 100b.

In FIG. 3, finally, the effectiveness of the method, according to the invention, is shown for a real clinical case, in particular a magnetic resonance image of the brain of a patient. By comparing the starting images 100a and 100b, respectively obtained with phase encoding for columns and phase encoding for rows, with the image 100c, is clear how the method according to the invention allows to improve the quality of the magnetic resonance image by completely eliminating the aliasing artifacts. Therefore, the method according to the invention is able to provide a magnetic resonance image, which will make the doctor able to draft a very accurate report highlighting with absolute certainty the presence of any possible pathology in act, thus eliminating the need of repeating the examination in order to overcome any doubts owing to a low quality of the image.

The invention claimed is:

1. A method for eliminating aliasing artifacts, in a magnetic resonance image, said method comprising the steps of:
   obtaining a first starting image acquired by a determined acquisition sequence and using a phase encoding for columns, said first starting image being organized according to a matrix structure m-n comprising a plurality of portions arranged according to m rows and n columns, wherein each portion of said plurality of portions of said first starting image is associated to a numerical value corresponding to a light intensity of said portion of said first starting image;
   obtaining a second starting image obtained through said determined acquisition sequence used for obtaining said first starting image but using a phase encoding for rows, said second starting image being organized according to the matrix structure m-n comprising the plurality of portions arranged according to m rows and n columns, wherein each portion of said plurality of portions of said second starting image is associated to a numerical value corresponding to a light intensity of said portion of said second starting image;
   comparing said numerical values of each portion of said first starting image with a homologous portion of said second starting image which occupies the same position in the matrix structure m-n of the first and the second starting images;
   constructing a new matrix structure comprising the plurality of portions arranged according to m rows and n columns, said constructing step comprising:
   computing a difference of the numerical values of each couple of homologous portions of said first and of said second starting images;
   associating to a portion of said new matrix structure homologous to said portions of said first and of said second starting image, the numerical value of the homologous portion of the first starting image, or of an average value of the numerical values of said homologous portions, if said difference is less than a predetermined threshold value, or, alternatively, associating to said portion the smaller numerical value between the numerical values of said first and of said second homologous portion, if said difference is greater than said predetermined threshold value,
   iterating the above steps for each couple of homologous portions of said first and of said second starting image in such a way to obtain a new matrix structure corresponding to an improved magnetic resonance image;
   wherein, before said comparing step, a translating step is provided for translating at least one of said first and said second starting images with respect to a reference system, in order to minimize the differences among the numerical values of the homologous portions of said first and of said second starting images owing to the fact that said first and said second starting images are obtained with a different phase encoding.

2. The method according to claim 1, wherein said translating step is carried out according to the results of a preliminary measuring step in which the numerical value is determined of each portion of said first and of said second starting image, and of a following comparing step of the numerical values of the homologous portions.

3. The method according to claim 2, wherein said preliminary measuring step comprises the steps of:
   carrying out a plurality of determined translations of at least one between said first and said second starting images;
   computing a mean squared error of the difference of the numerical values of said first and of said second starting image for each determined translating step of said plurality of determined translations; and
   selecting the translation among said plurality of determined translations corresponding to the smaller computed value of the mean squared error.

* * * * *